US012635956B2

(12) United States Patent
Bayram

(10) Patent No.: US 12,635,956 B2
(45) Date of Patent: May 26, 2026

(54) DECOMPOSITION OF COMPOSITE SIGNALS

(71) Applicant: Analog Devices, Inc., Norwood, MA (US)

(72) Inventor: Ilker Bayram, Brookline, MA (US)

(73) Assignee: Analog Devices, Inc., Wilmington, MA (US)

( * ) Notice: Subject to any disclaimer, the term of this patent is extended or adjusted under 35 U.S.C. 154(b) by 324 days.

(21) Appl. No.: 17/025,696

(22) Filed: Sep. 18, 2020

(65) Prior Publication Data

US 2022/0087618 A1 Mar. 24, 2022

(51) Int. Cl.
| | |
|---|---|
| *A61B 5/00* | (2006.01) |
| *A61B 5/0205* | (2006.01) |
| *G16H 50/30* | (2018.01) |
| *A61B 5/08* | (2006.01) |

(52) U.S. Cl.
CPC .......... *A61B 5/7278* (2013.01); *A61B 5/0205* (2013.01); *A61B 5/7203* (2013.01); *G16H 50/30* (2018.01); *A61B 5/08* (2013.01)

(58) Field of Classification Search
CPC ... A61B 5/7278; A61B 5/0205; A61B 5/7203; A61B 5/08; A61B 5/7246; A61B 5/725; A61B 5/6823; A61B 5/0255; A61B 5/0507; A61B 5/0803; G16H 50/30; G16H 50/20
See application file for complete search history.

(56) References Cited

U.S. PATENT DOCUMENTS

| | | | | |
|---|---|---|---|---|
| 6,862,558 | B2 | 3/2005 | Huang | |
| 7,519,488 | B2 | 4/2009 | Fu et al. | |
| 9,818,416 | B1 * | 11/2017 | Kamen | ................. G10L 21/038 |
| 2003/0098971 | A1 * | 5/2003 | Laffont | .................. G01N 21/45 |
| | | | | 356/128 |
| 2008/0300499 | A1 * | 12/2008 | Strube | .................... A61B 5/113 |
| | | | | 600/534 |
| 2011/0245628 | A1 * | 10/2011 | Baker, Jr. | ............. A61B 5/0205 |
| | | | | 600/300 |
| 2012/0310600 | A1 * | 12/2012 | Pao | ........................... A61B 5/30 |
| | | | | 702/189 |
| 2015/0216475 | A1 * | 8/2015 | Luna | .................... A61B 5/7278 |
| | | | | 600/301 |

OTHER PUBLICATIONS

Bayram, *An Exploratory Method for Smooth/Transient Decomposition*, IEEE, May 6, 2020, 8 pages.
He et al., "Adaptive Separation of Respiratory and Heartbeat Signals among Multiple People Based on Empirical Wavelet Transform Using UWB Radar," Sensors (Basel). Aug. 31, 2020; 20(17):4913.

* cited by examiner

*Primary Examiner* — Sana Sahand
(74) *Attorney, Agent, or Firm* — ArentFox Schiff LLP

(57) ABSTRACT
Disclosed herein are example systems and approaches for decomposition of composite signals. Decomposition of the composite signals may include derivation of two or more signals from the composite signals. An upper envelope and lower envelope may be determined for a composite signal in accordance with a smoothness parameter. A smooth estimate may be produced based on the upper envelope and the lower envelope, where the smooth estimate provides an estimate for a smooth component of the composite signal, which may be more accurate than legacy approaches.

11 Claims, 9 Drawing Sheets

400

402 OBTAIN COMPOSITE SIGNAL

404 PRODUCE UPPER ENVELOPE

406 PRODUCE LOWER ENVELOPE

408 PRODUCE SMOOTH ESTIMATE

410 PRODUCE TRANSIENT ESTIMATE

DECOMPOSITION OF COMPOSITE SIGNALS

FIELD OF THE DISCLOSURE

This disclosure relates in general to the field of signal processing, and more particularly, though not exclusively, to a system and method for decomposing a composite signal.

BACKGROUND

It may be desirable in signal processing to analyze individual signals, however, the means for producing a signal may produce a composite signal, where the composite signal is a combination representing two or more signals. For example, a sensor (such as a radar sensor) monitoring vital signs of an individual may produce a composite signal produced by a combination of a first signal (such as a signal representing heart beats) and a second signal (such as a signal representing respiration). When processing the composite signal, it can be beneficial to separate out the signals from the composite signal for processing. Separating out the individual signals from the composite signal can be a challenge.

BRIEF DESCRIPTION OF THE DRAWINGS

The present disclosure is best understood from the following detailed description when read with the accompanying figures. It is emphasized that, in accordance with the standard practice in the industry, various features are not necessarily drawn to scale, and are used for illustration purposes only. Where a scale is shown, explicitly or implicitly, it provides only one illustrative example. In other embodiments, the dimensions of the various features may be arbitrarily increased or reduced for clarity of discussion.

SUMMARY OF THE DISCLOSURE

Figure 1:
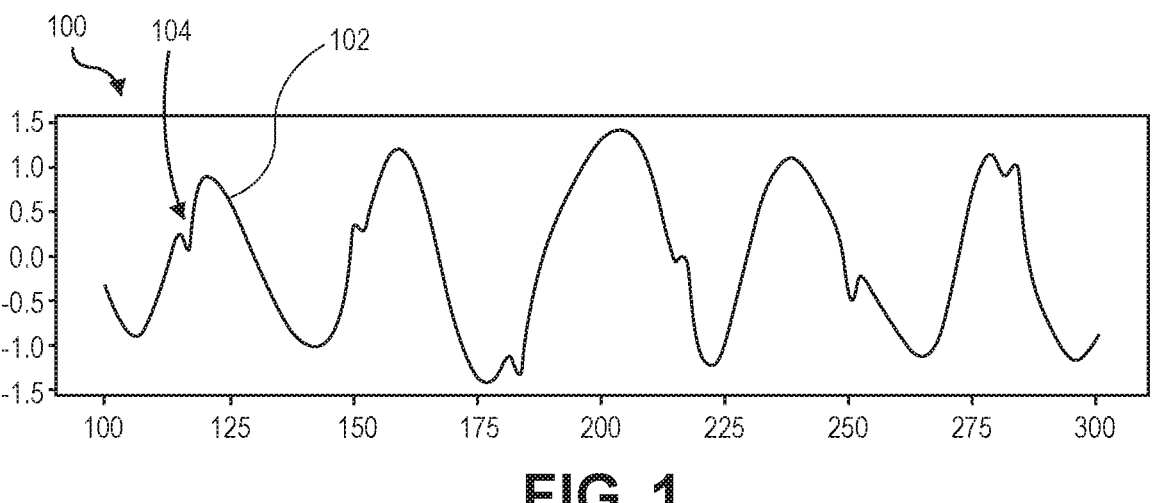
FIG. 1 illustrates a graph of an example composite signal, according to various embodiments of the disclosure.

Disclosed herein are example systems and approaches for decomposition of composite signals. Decomposition of the composite signals may include derivation of two or more signals from the composite signals. An upper envelope and lower envelope may be determined for a composite signal in accordance with a smoothness parameter. A smooth estimate may be produced based on the upper envelope and the lower envelope, where the smooth estimate provides an estimate for a smooth component of the composite signal, which may be more accurate than legacy approaches.

Some embodiments described herein may include one or more computer-readable media. The computer-readable media may have instructions stored thereon, wherein the instructions, when executed by a device, cause the device to produce an upper envelope for a composite signal and produce a lower envelope for the composite signal. The instructions may further cause the device to produce a smooth estimate for a smooth component of the composite signal, the smooth estimate to be located between the upper envelope and the lower envelope.

Some embodiments described herein may include a method for decomposition of a composite signal. The method may include obtaining the composite signal for decomposition, producing an upper envelope based on the composite signal, the upper envelope meeting a smoothness criteria, and producing a lower envelope based on the composite signal, the lower envelope meeting the smoothness criteria. The method may further include producing a smooth estimate of a smooth component of the composite signal, the smooth estimate located between the upper envelope and the lower envelope.

Some embodiments described herein may include a vital monitor system, comprising a sensor to sense vital signs of an individual, and generate a composite signal based on the vital signs. The vital monitor system may further include a device coupled to the sensor, the device to obtain the composite signal from the sensor, produce an upper envelope based on the composite signal in accordance with a smoothness parameter, and produce a lower envelope based on the composite signal in accordance with the smoothness parameter. The device may further be to produce a smooth estimate for a smooth component of the composite signal, wherein the smooth estimate is to be located between the upper envelope and the lower envelope, and wherein the smooth estimate corresponds to a vital sign of the vital signs.

DETAILED DESCRIPTION

The systems and approaches described herein may be utilized for signal processing of a composite signal, where the composite signal may be formed by a combination of two or more signals. For example, the composite signal may comprise a plurality of signals with each of the plurality of signals can relate to a different property. The composite signal described herein may be produced by radar sensor sensing vital signs of an individual, where the vital signs may include respiration of the individual and heart activity of the individual. In particular, the composite signal may be decomposed into a first signal corresponding to the respiration of the individual and a second signal corresponding to the heart activity of the individual. The first signal corresponding to the respiration may comprise a smooth signal while the second signal corresponding to the heart activity may comprise a transient, non-smooth signal.

The signal processing approach described herein may utilize upper envelopes and lower envelopes for generating an estimate of the first signal. In particular, the upper envelope and the lower envelope may both be smooth signals that have the composite signal located between the upper envelope and the lower envelope. The estimate may comprise a smooth estimate located between the upper envelope and the lower envelope. The smooth estimate may be an estimate of the first signal component of the composite signal. The smooth estimate may be a more accurate estimate of a smooth signal than legacy approaches for estimating a smooth signal. Accordingly, the approach may provide for more accurate data for determining respiration of the individual in the presented instance. Further, a difference between the smooth estimate and the composite signal may be utilized to produce the second signal corresponding to the heart activity in the presented instance, which can result in more accurate data for determining the heart activity of the individual.

FIG. 1 illustrates a graph 100 of an example composite signal 102, according to various embodiments of the disclosure. The composite signal 102 is one example of a composite signal to which the approaches described herein may be applied. The composite signal 102 may be produced by a sensor, such as a radar sensor.

The composite signal 102 may be decomposed into one or more signals that each may correspond to different characteristics sensed by the sensor. The one or more signals may provide different characteristics to the composite signal 102. For example, the composite signal 102 illustrated is mostly smooth with some deviations (such as deviation 104) from the smoothness. The smooth characteristic of the composite signal 102 may be provided by a first characteristic sensed by the sensor and the deviations of the composite signal 102 may be provided by a second characteristic sensed by the sensor. Decomposition of the composite signal 102 may provide for evaluation of the first characteristic sensed by the sensor and the second characteristic sensed by the sensor. Accordingly, the composite signal 102 may be decomposed into a first signal that is smooth and can correspond to the first characteristic sensed by the sensor, and a second signal that is transient and can correspond to the second characteristic sensed by the sensor. The second signal may be a transient, non-smooth signal.

Figure 2:
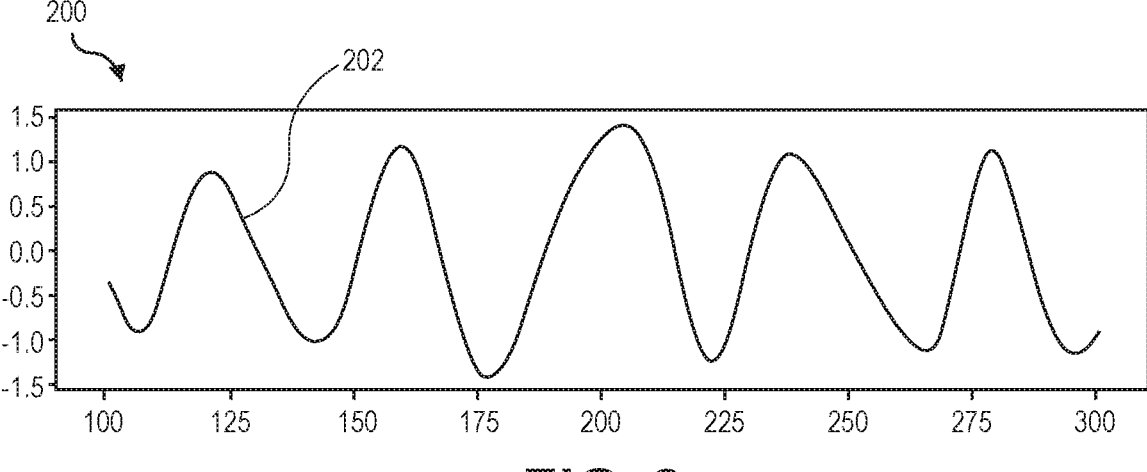
FIG. 2 illustrates a graph of an example smooth signal, according to various embodiments of the disclosure.

FIG. 2 illustrates a graph 200 of an example smooth signal 202, according to various embodiments of the disclosure. The smooth signal 202 may contribute the smoothness characteristic to the composite signal 102 (FIG. 1). Accordingly, the smooth signal 202 may be a signal which is desired to be derived from the composite signal 102 for analysis. The smooth signal 202 may correspond to a first characteristic sensed by the sensor. By deriving the smooth signal 202 from the composite signal 102, the smooth signal 202 may be analyzed for making determinations regarding the first characteristic. The smooth signal 202 may be one of the signals that may be estimated by the approaches described herein based on the composite signal 102. In some embodiments, the first characteristic may be respiration of an individual, where the smooth signal 202 may correspond to the respiration of the individual.

Figure 3:
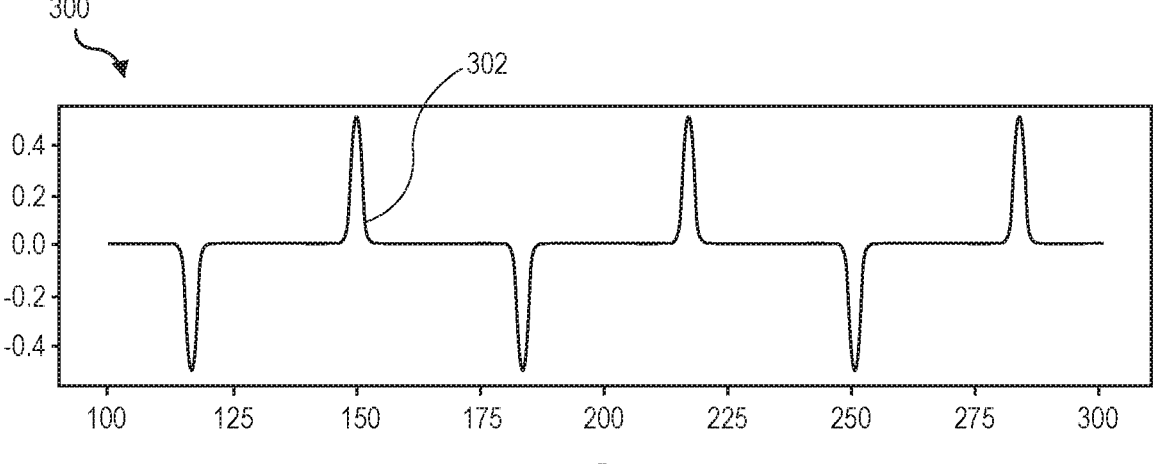
FIG. 3 illustrates a graph of an example transient signal, according to various embodiments of the disclosure.

FIG. 3 illustrates a graph 300 of an example transient signal 302, according to various embodiments of the disclosure. The transient signal 302 may comprise a transient, non-smooth signal. The transient signal 302 may contribute the deviations to the composite signal 102 (FIG. 1). Accordingly, the transient signal 302 may be a signal which is desired to be derived from the composite signal 102 for analysis. The transient signal 302 may correspond to a second characteristic sensed by the sensor. By deriving the transient signal 302 from the composite signal 102, the transient signal 302 may be analyzed for making determinations regarding the second characteristic. The transient signal 302 may be one of the signals that may be estimated by the approaches described herein based on the composite signal 102. In some embodiments, the second characteristic may be heart activity of the individual, where the transient signal 302 may correspond to the heart activity of the individual. While the composite signal 102 is described as having two signals (i.e., the smooth signal 202 and the transient signal 302) contributing to the composite signal 102 and being derivable from the composite signal 102, it should be understood that there may be more than two signals that contribute to a composite signal and/or are derivable from the composite signal in other embodiments.

Figure 4:
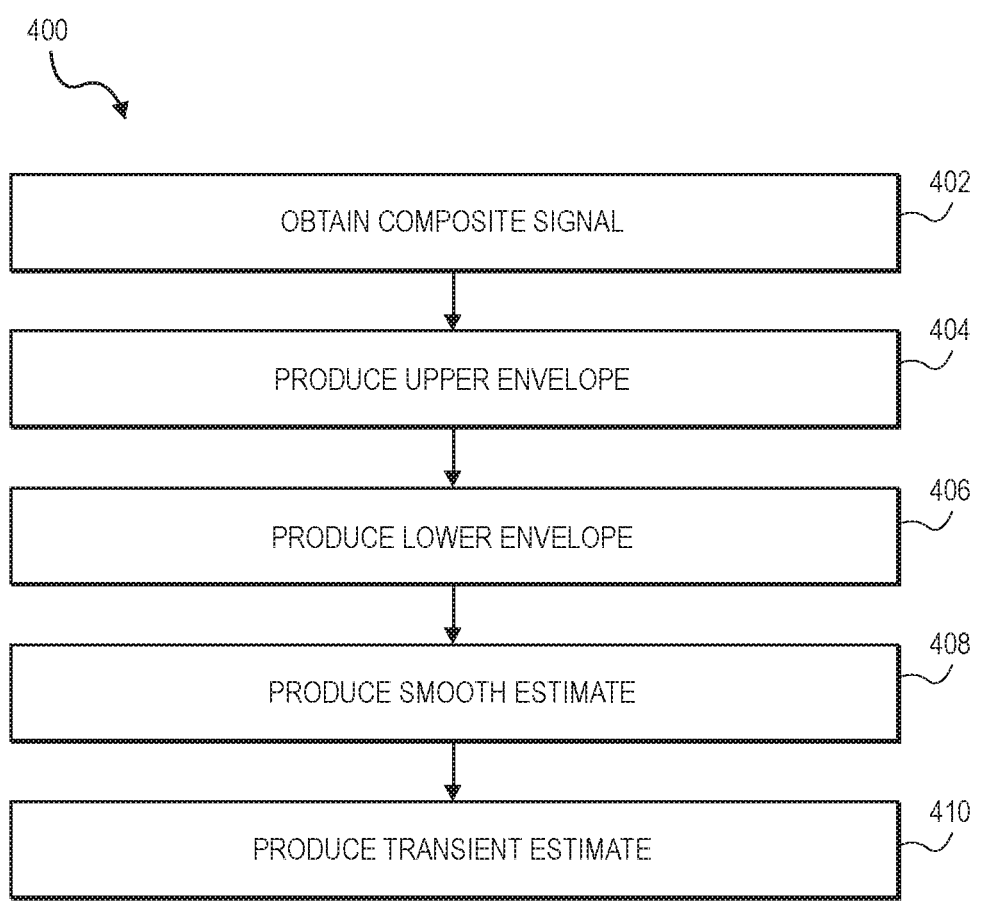
FIG. 4 illustrates an example procedure for decomposition of a composite signal, according to various embodiments of the disclosure.

FIG. 4 illustrates an example procedure 400 for decomposition of a composite signal, according to various embodiments of the disclosure. The procedure 400 may be applied to a composite signal and may derive one or more signals from the composite signal. For example, the procedure 400 may be applied to the composite signal 102 (FIG. 1) to produce estimates of the smooth signal 202 (FIG. 1) and the transient signal 302 (FIG. 3). The signals produced by the procedure 400 may be analyzed to make determinations about one or more characteristics.

In 402, a composite signal may be obtained. For example, the composite signal may be obtained from a sensor or a memory device. In some instances, the composite signal may be provided to the device performing the procedure 400. The composite signal may be decomposable into two or more signals, where each of the signals may correspond to a characteristic. For example, a sensor that produces the composite signal may sense multiple characteristics, where each characteristic corresponds to a signal that contributes to the composite signal.

Figure 5:
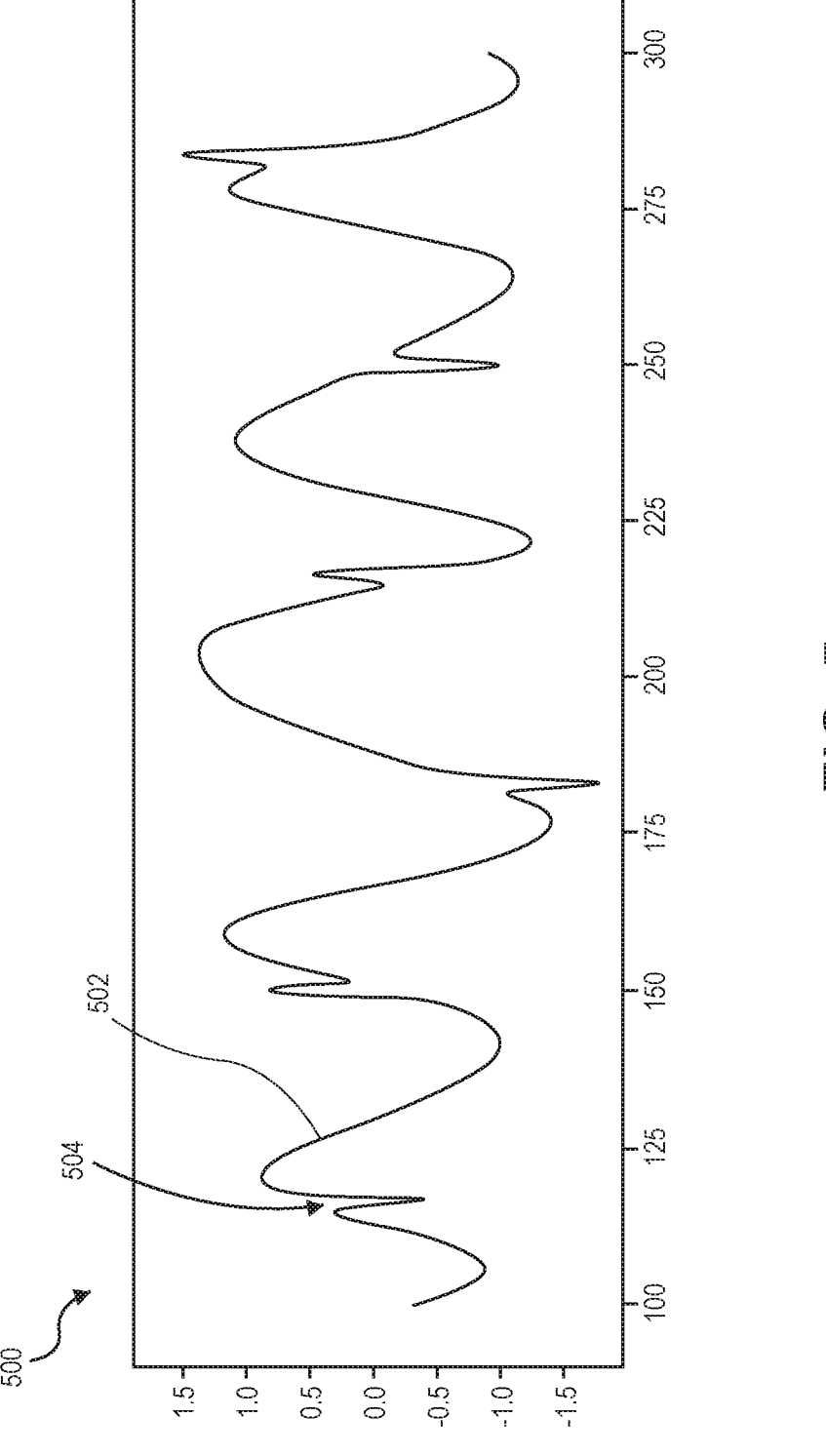
FIG. 5 illustrates a graph of an example composite signal, according to various embodiments of the disclosure.

FIG. 5 illustrates a graph 500 of an example composite signal 502, according to various embodiments of the disclosure. The composite signal 502 is an example of a composite signal that may be obtained by the procedure 400 in 402. As can be seen, the composite signal 502 is mostly smooth with some deviations (such as deviation 504). The composite signal 502 may have been produced by a sensor, such as a radar sensor. In particular, the composite signal 502 may be produced by a radar sensor sensing vital signs of an individual. In the illustrated instance, the radar sensor may have detected chest displacement of the individual, where the chest displacement may be due to the characteristics of respiration of the individual and heart activity of the individual. Accordingly, the respiration and the heart activity of the individual may contribute to the composite signal 502, where a first signal corresponding to the respiration and a second signal corresponding to the heart activity may be derived from the composite signal 502. The first signal corresponding to the respiration may be a smooth signal due to the continuous rhythmic nature of the respiration, whereas the second signal corresponding to the heart activity may be a transient, non-smooth signal due to the transient rhythmic nature of the heart activity. Further, the respiration may have a stronger influence on the chest displacement than the heart activity, causing the amplitude of the smooth signal corresponding to the respiration to have a greater amplitude than the transient signal corresponding to the heart activity. These characteristics of the smooth signal and the transient signal are presented by the composite signal 502, where the smooth component has a greater effect on the amplitude of the composite signal 502 than the transient component that causes the deviations.

In 404, an upper envelope may be produced. The upper envelope may be produced based on the composite signal obtained in 402. The upper envelope may comprise a curve, where lower limits of the curve can be set to the composite signal. A Gaussian process (GP) may be utilized to produce the upper envelope. The GP may be set with a smoothness parameter, where the smoothness parameter may set a smoothness characteristic for the upper envelope. For example, the smoothness parameter may set a maximum change in the slope of the upper envelope that may occur. It should be understood that this is a single example of a smoothness parameter, and the smoothness parameter may define other limitations related to the smoothness for the upper envelope.

The upper envelope may be obtained by solving the following minimization problem:

$$\min_x \frac{\lambda}{2}\|y - x\|_2^2 + S_\sigma(x)$$

subject to $a_i \leq x_i \leq b_i$, where $\lambda$ may be a weight parameter; y may be a vector containing an observation of the composite signal (such as the composite signal 502) (which may be referred to as an observation); x may be a variable vector over which the search for the upper envelope is performed; $S_o(\cdot)$ may be a function taking high values when its input deviates from being smooth, with the parameter a controlling the amount of smoothness; and $a_i$ and $b_i$ set a range for the values of the envelope (i.e., x). x may be a sample from a zero-mean GP with a covariance given as:

$$C_\sigma(x_n, x_m) = \begin{cases} 0, \text{ if } \exp(-(n-m)^2/\sigma^2)/\tau \\ \exp(-(n-m)^2/\sigma^2, \text{ otherwise} \end{cases},$$

where $\tau > 0$ is a threshold. The upper envelope may be produced by setting $a_i = y$ and $b_i = \infty$ and solving the minimization problem. The smoothness parameter may further be set for providing a different amount of smoothness for the upper envelope.

Figure 6:
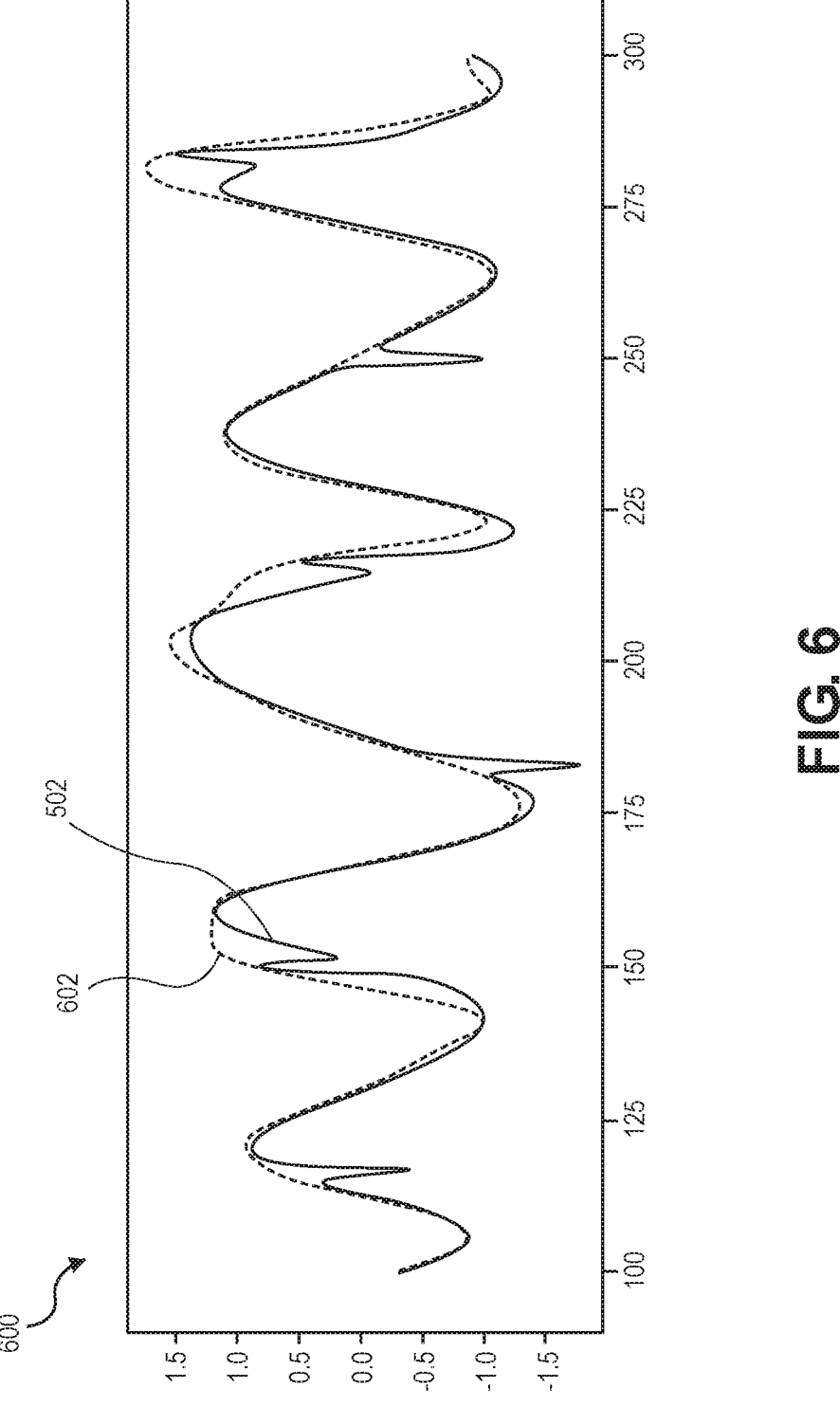
FIG. 6 illustrates a graph of an example upper envelope, according to various embodiments of the disclosure.

FIG. 6 illustrates a graph 600 of an example upper envelope 602, according to various embodiments of the disclosure. In particular, the upper envelope 602 shown may be produced by the procedure 400 in 404 based on the composite signal 502. The upper envelope 602 may be equal to or greater than the composite signal 502. The upper envelope 602 may follow the composite signal 502 while maintaining the maximum amount of smoothness and remaining equal to or greater than the composite signal 502. For example, the upper envelope 602 may have positive and negative peaks that occur in similar locations to the positive and negative peaks of the composite signal 502 while maintaining the smoothness set by the smoothness parameter. The upper envelope 602 may be located as close as possible to the composite signal 502 while being greater than or equal to the composite signal 502 and fulfilling the smoothness criteria defined by the smoothness parameter in some embodiments.

In 406, a lower envelope may be produced. The lower envelope may be produced based on the composite signal obtained in 402. The lower envelope may comprise a curve, where upper limits of the curve can be set to the composite signal. A GP may be utilized to produce the lower envelope. The GP may be set with a smoothness parameter, where the smoothness parameter may set a smoothness characteristic for the lower envelope. The smoothness parameter may be equal to the smoothness parameter for the upper envelope or may be different from the smoothness parameter for the upper envelope. The smoothness parameter may set a maximum change in the slope of the lower envelope that may occur. It should be understood that this is a single example of a smoothness parameter, and the smoothness parameter may define other limitations related to the smoothness of the lower envelope.

The equation for defining the lower envelope may be of the same form as the equation for defining the upper envelope. In particular, the lower envelope may be obtained by solving the following minimization problem:

$$\min_x \frac{\lambda}{2}\|y - x\|_2^2 + S_\sigma(x)$$

subject to $a_i \leq x_i \leq b_i$, where $\lambda$ may be a weight parameter; y may be a vector containing in observation of the composite signal (such as the composite signal 502) (which may be referred to as an observation); x may be a variable vector over which the search for the lower envelope is performed; $S_o(\cdot)$ may be a function taking high values when its input deviates from being smooth, with the parameter a controlling the amount of smoothness; and $a_i$ and $b_i$ set a range for the values of the envelope (i.e., x). x may be a sample from a zero-mean GP with a covariance given as:

$$C_\sigma(x_n, x_m) = \begin{cases} 0, \text{ if } \exp(-(n-m)^2/\sigma^2)/\tau \\ \exp(-(n-m)^2/\sigma^2, \text{ otherwise} \end{cases},$$

where $\tau > 0$ is a threshold. The lower envelope may be produced by setting $a_i = -\infty$ and $b_i = y$ and solving the minimization problem. The smoothness parameter may further be set for providing a different amount of smoothness for the lower envelope. The smoothness parameter for the lower envelope may be the same as the smoothness parameter for the upper envelope or may be different from the smoothness parameter for the upper envelope.

Figure 7:
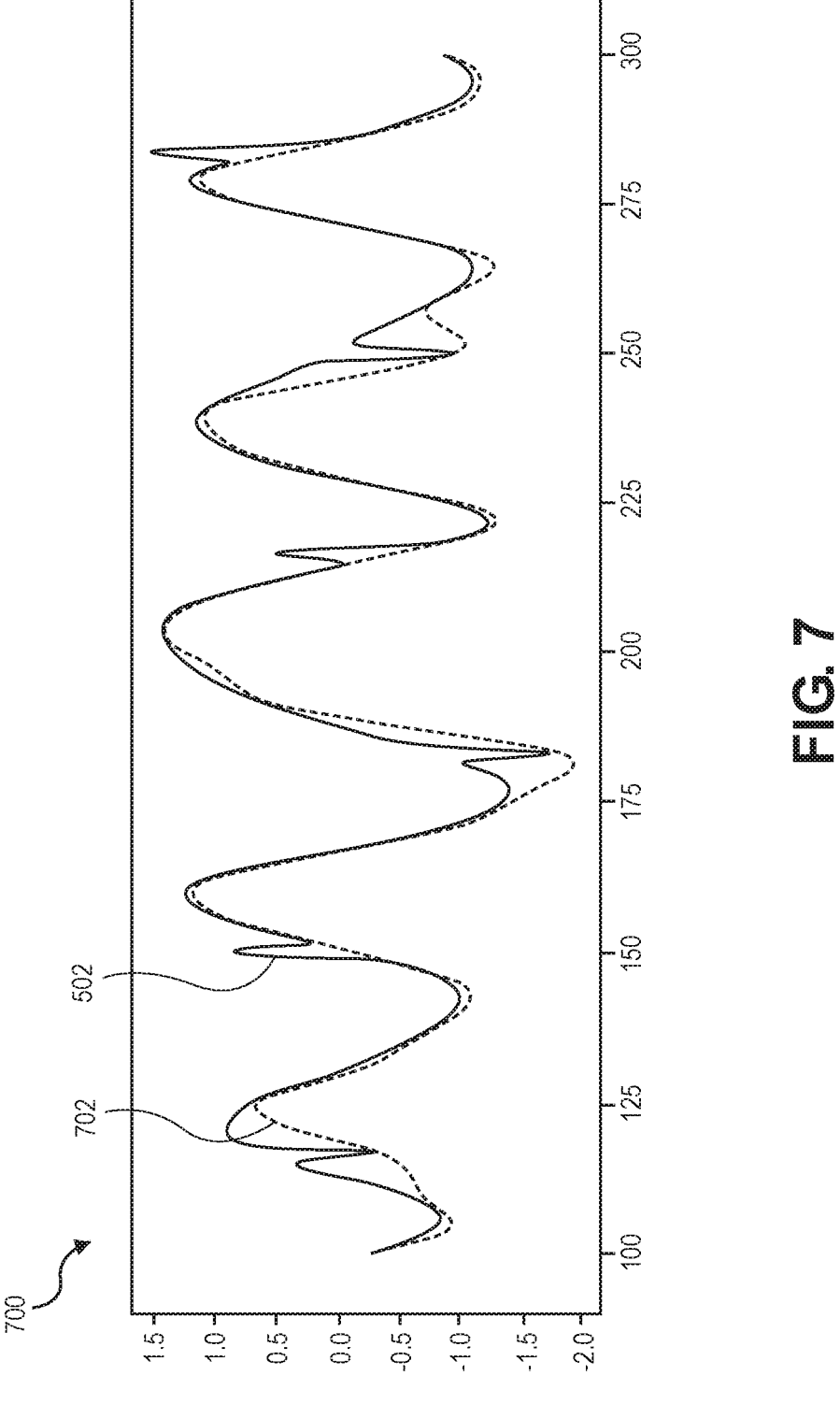
FIG. 7 illustrates a graph of an example lower envelope, according to various embodiments of the disclosure.

FIG. 7 illustrates a graph 700 of an example lower envelope 702, according to various embodiments of the disclosure. In particular, the lower envelope 702 may be produced by the procedure 400 in 406 based on the composite signal 502. The lower envelope 702 may be equal to or less than the composite signal 502. The lower envelope 702 may follow the composite signal 502 while maintaining the maximum amount of smoothness and remaining equal to or greater than the composite signal 502. For example, the lower envelope 702 may have positive and negative peaks that occur in similar locations to the positive and negative peaks of the composite signal 502 while maintaining the smoothness defined by the smoothness parameter. The lower envelope 702 may be located as close as possible to the composite signal 502 while being less than or equal to the composite signal 502 and fulfilling the smoothness criteria defined by the smoothness parameter in some embodiments.

In 408, a smooth estimate may be produced. The smooth estimate may be produced based on the upper envelope and the lower envelope. The smooth estimate may comprise a curve, where upper limits of the curve can be set to the upper envelope and lower limits of the curve can be set to the lower envelope. A GP may be utilized to produce the smooth estimate. The GP may be set with a smoothness parameter, where the smoothness parameter may set a smoothness characteristic of the smooth estimate. The smoothness parameter may be equal to the smoothness parameter for the upper envelope, equal to the smoothness parameter for the lower envelope, equal to the smoothness parameter for both the upper envelope and the lower envelope, or different from the smoothness parameter for the upper envelope and the lower envelope. The smoothness parameter may set a maximum change in the slope of the smooth estimate that may occur. It should be understood that this is a single example of a smoothness parameter, and the smoothness parameter may define other limitations related to the smoothness of the smooth estimate.

The equation for defining the smooth estimate may be of the same form as the equation for defining the upper envelope and the lower envelope. In particular, the smooth estimate may be obtained by solving the following minimization problem:

$$\min_{x} \frac{\lambda}{2} \|y - x\|_2^2 + S_\sigma(x)$$

subject to $a_i \leq x_i \leq b_i$, where $\lambda$ may be a weight parameter; y may be a vector containing an observation of the composite signal (such as the composite signal 502) (which may be referred to as an observation); x may be a variable vector over which the search for the smooth estimate is performed; $S_\sigma(\cdot)$ may be a function taking high values when its input deviates from being smooth, with the parameter a controlling the amount of smoothness; and $a_i$ and $b_i$ set a range for the values of the envelope (i.e., x). For the smooth estimate, the weight parameter, $\lambda$, may be set lower than the weight parameter utilized for determination of the upper envelope and the lower envelope to reduce the direct influence of the composite signal on the smooth estimate in some embodiments. Further, a for controlling the amount of smoothness may be set to be greater for the smooth estimate than for upper envelope and the lower envelope to relax the amount of required smoothness in some embodiments. The smooth estimate may be produced by setting $a_i$=l, where l is the lower envelope, and $b_i$=u, where u is the upper envelope. In other words, the smooth estimate may be produced by solving the minimization problem with the maximum set to the upper envelope and the minimum set to the lower envelope.

Figure 8:
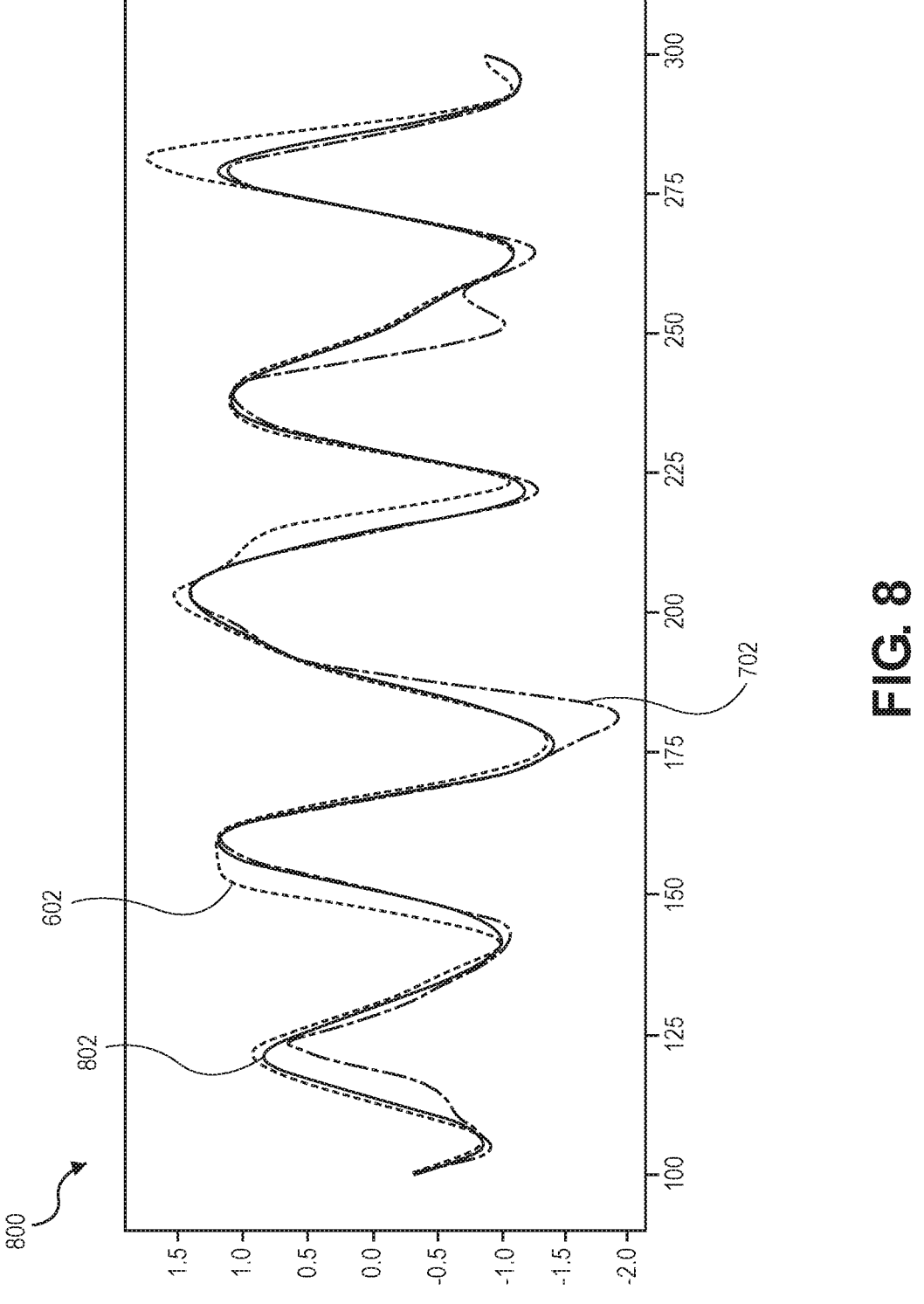
FIG. 8 illustrates a graph of an example smooth estimate with the example upper envelope of FIG. 6 and the example lower envelope of FIG. 7, according to various embodiments of the disclosure.
Figure 9:
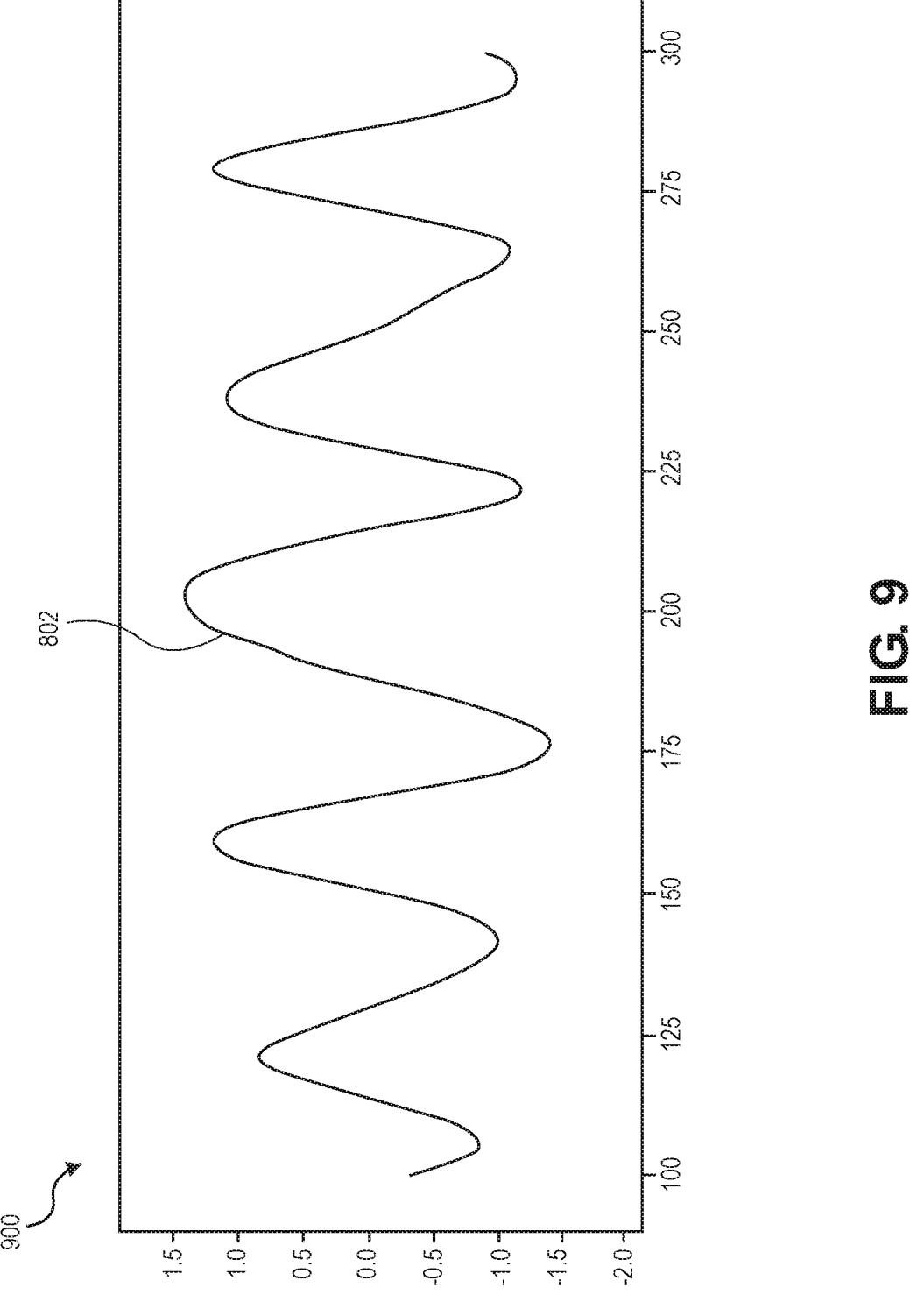
FIG. 9 illustrates a graph of the example smooth estimate, according to various embodiments of the disclosure.

FIG. 8 illustrates a graph 800 of an example smooth estimate 802 with the example upper envelope 602 of FIG. 6 and the example lower envelope 702 of FIG. 7, according to various embodiments of the disclosure. FIG. 9 illustrates a graph 900 of the example smooth estimate 802, according to various embodiments of the disclosure. In particular, graph 900 illustrates the example smooth estimate 802 without the upper envelope 602 and the lower envelope 702 for clarity. The smooth estimate 802 may be produced by the procedure 400 in 408 based on the upper envelope 602 and the lower envelope 702. The smooth estimate 802 may be located between the upper envelope 602 and the lower envelope 702. In particular, the smooth estimate 802 may be less than or equal to the upper envelope 602 and greater than or equal to the lower envelope 702. A smoothness of the smooth estimate 802 may maintain the maximum amount of smoothness defined by the smoothness parameter for the smooth estimate 802. The smooth estimate 802 may be an estimate of a smooth component of the composite signal 502 (FIG. 5). In particular, the composite signal 502 may be decomposed into two signals that contribute to the composite signal 502 as mentioned. The first signal may be a smooth signal, which contributes a smooth component to the composite signal 502. The smooth estimate 802 may be an estimate for the smooth signal. The smooth estimate 802 may be a more accurate estimate for the smooth signal than can be provided by legacy approaches. In the presented example, the smooth estimate 802 may be an estimate for the signal corresponding to the respiration of the individual. Accordingly, the smooth estimate 802 may be analyzed to determine characteristics of the respiration of the individual.

In 410, a transient estimate may be produced. The transient estimate may be produced based on a comparison of the smooth estimate with the composite signal. In particular, the difference between the smooth estimate and the composite signal may be determined, where the difference may comprise the transient estimate. In some instances, further processing may be applied to the difference between the smooth estimate and the composite signal, such as filtering differences below a certain amplitude and/or filtering certain frequencies. In some embodiments, 410 may be omitted.

Figure 10:
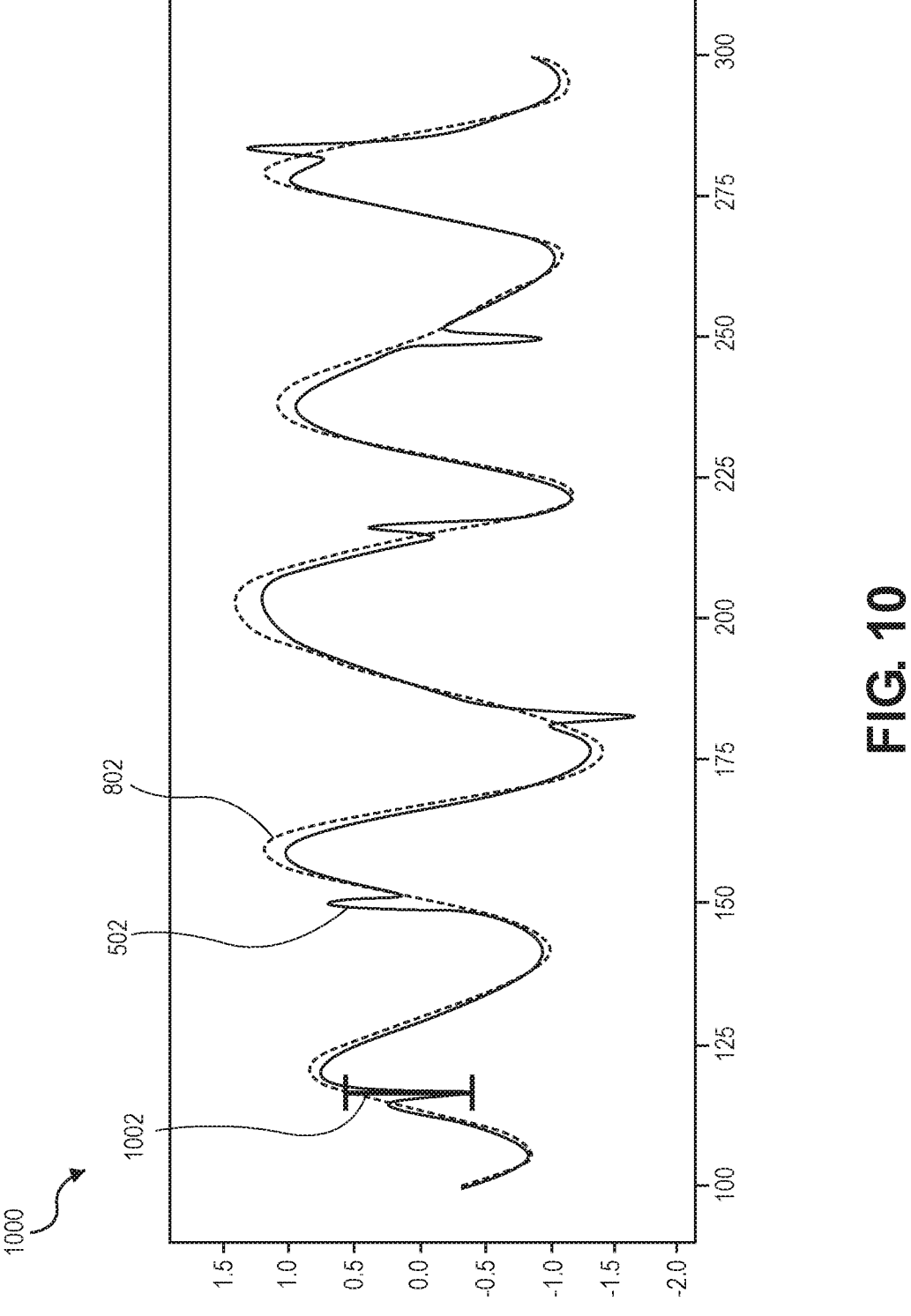
FIG. 10 illustrates a graph showing the production of an example transient estimate, according to various embodiments of the disclosure.

FIG. 10 illustrates a graph 1000 showing the production of an example transient estimate, according to various embodiments of the disclosure. The graph shows the composite signal 502 and the smooth estimate 802. The difference 1002 (shown at a single position along the signals for clarity) between the composite signal 502 and the smooth estimate 802 may be determined. The difference 1002 may define a transient estimate for the transient component of the composite signal 502. For example, the transient estimate may be an estimate for a transient signal (such as the transient signal 302 (FIG. 3)) that may be derived from the composite signal 502. The difference 1002 may be utilized to produce a curve that comprises the transient estimate.

Figure 11:
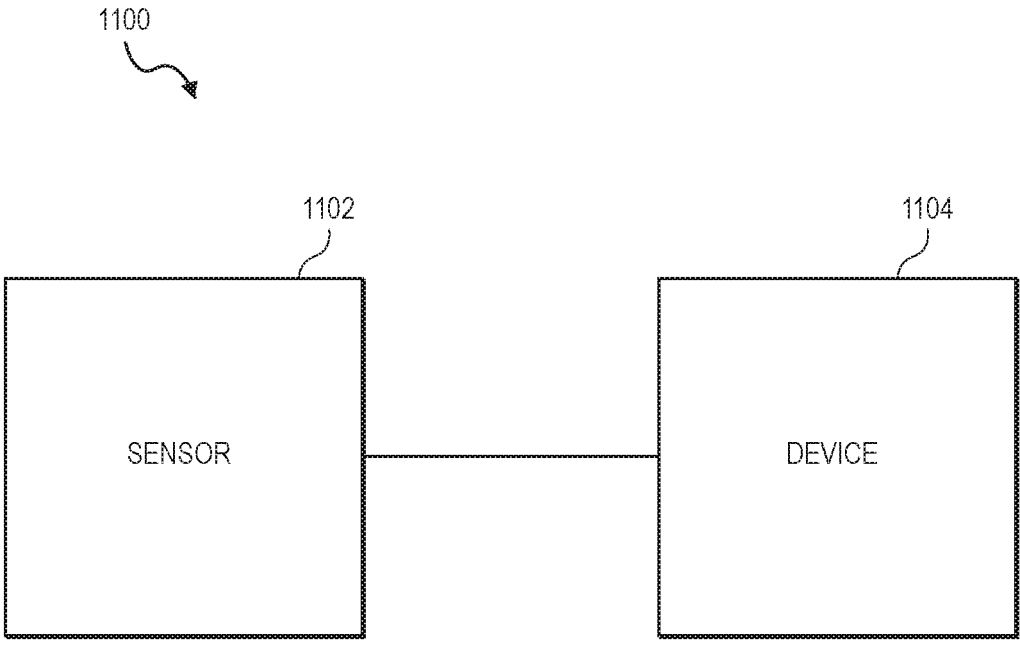
FIG. 11 illustrates an example system that may implement the procedure of FIG. 4, according to various embodiments of the disclosure.

FIG. 11 illustrates an example system 1100 that may implement the procedure 400 of FIG. 4, according to various embodiments of the disclosure. In particular, the system 1100, or portions thereof, may perform the procedure 400.

The system 1100 may include a sensor 1102. The sensor 1102 may sense some characteristics and output a signal based on the characteristics. For example, the sensor 1102 may comprise a radar sensor in some embodiments. The radar sensor may sense vital signs of an individual and output a signal based on the vital signs. The characteristics sensed by the sensor 1102 in some instances may relate to two or more characteristics, where the two or more characteristics may contribute different components to a signal output by the sensor 1102. Accordingly, the signal output by the sensor 1102 may comprise a composite signal (such as the composite signal 102 (FIG. 1) and/or the composite signal 502 (FIG. 5)) in these instances, where two or more signals corresponding to the two or more characteristics may be derived from the composite signal. In the embodiments where the sensor 1102 is a radar sensor that senses the vital signs of the individual, the characteristics sensed by the radar sensor may include respiration of the individual and heart activity of the individual. Signals corresponding to the respiration of the individual and the heart activity of the individual may be derived from the composite signal. The sensor 1102 may output the composite signal.

The system 1100 may further include a device 1104. In some embodiments, the device 1104 may comprise a computer system, a microprocessor, signal processing circuitry, or some combination thereof. The device 1104 may be coupled to the sensor 1102 and may receive the composite signal output by the sensor 1102. The device 1104 may perform the procedure 400 on the composite signal to derive one or more signals from the composite signal. For example, the device 1104 may derive a first signal corresponding to the respiration of the individual and/or a second signal corresponding to the activity of the individual in embodiments where the sensor 1102 is the radar sensor sensing vital signs of the individual.

While the sensor 1102 and the device 1104 are described as separate entities in the illustrated embodiment, it should be understood that the sensor 1102 and the device 1104 may be located within a single entity in other embodiments. Further, in other embodiments, the device 1104 may perform a portion of the procedure 400 while the sensor 1102 and/or other devices perform other portions of the procedure 400.

Example Implementations

The following examples are provided by way of illustration.

Example 1 may include one or more computer-readable media having instructions stored thereon, wherein the instructions, when executed by a device, cause the device to produce an upper envelope for a composite signal, produce a lower envelope for the composite signal, and produce a smooth estimate for a smooth component of the composite signal, the smooth estimate to be located between the upper envelope and the lower envelope.

Example 2 may include the one or more computer-readable media of example 1, wherein to produce the upper envelope includes to produce a first curve with lower limits set by the composite signal, and to produce the lower envelope includes to produce a second curve with upper limits set by the composite signal.

Example 3 may include the one or more computer-readable media of example 1, wherein the instructions, when executed by the device, further cause the device to set a smoothness parameter, wherein a smoothness of the smooth estimate is based on the smoothness parameter.

Example 4 may include the one or more computer-readable media of example 1, wherein the instructions, when executed by the device, further cause the device to set a smoothness parameter, wherein a smoothness of the upper envelope and a smoothness of the lower envelope is based on the smoothness parameter.

Example 5 may include the one or more computer-readable media of example 1, wherein to produce the upper envelope includes to solve a first minimization problem utilizing a first Gaussian process with a smoothness parameter and minimum set to the composite signal to produce the upper envelope, and to produce the lower envelope includes to solve a second minimization problem utilizing a second Gaussian process with the smoothness parameter and maximum set to the composite signal to produce the lower envelope.

Example 6 may include the one or more computer-readable media of example 1, wherein to produce the smooth estimate includes to solve a minimization problem utilizing a Gaussian process with a smoothness parameter, minimum set to the lower envelope, and maximum set to the upper envelope to produce the smooth estimate.

Example 7 may include the one or more computer-readable media of example 1, wherein the instructions, when executed by the device, further cause the device to generate a transient estimate for a transient component of the composite signal based on a difference between the smooth estimate and the composite signal.

Example 8 may include the one or more computer-readable media of example 7, wherein the smooth estimate corresponds to respiration of an individual and the transient estimate corresponds to heart activity of the individual.

Example 9 may include a method for decomposition of a composite signal, comprising obtaining the composite signal for decomposition, producing an upper envelope based on the composite signal, the upper envelope meeting a smoothness criteria, producing a lower envelope based on the composite signal, the lower envelope meeting the smoothness criteria, and producing a smooth estimate of a smooth component of the composite signal, the smooth estimate located between the upper envelope and the lower envelope.

Example 10 may include the method of example 9, wherein producing the upper envelope includes setting a minimum for the upper envelope to the composite signal, wherein the upper envelope is greater than or equal to the minimum, and producing the lower envelope includes setting a maximum for the lower envelope to the composite signal, wherein the lower envelope is less than or equal to the maximum.

Example 11 may include the method of example 9, further comprising setting a smoothness parameter, wherein the smoothness criteria is based on the smoothness parameter.

Example 12 may include the method of example 9, wherein the smooth estimate meets the smoothness criteria.

Example 13 may include the method of example 9, wherein producing the upper envelope includes solving a first minimization problem utilizing a first Gaussian process with the smoothness criteria and a minimum set to the composite signal to produce the upper envelope, and producing the lower envelope includes solving a second minimization problem utilizing a second Gaussian process with the smoothness criteria and a maximum set to the composite signal to produce the lower envelope.

Example 14 may include the method of example 9, wherein the smoothness criteria is a first smoothness criteria, and wherein producing the smooth estimate includes solving another minimization problem utilizing a Gaussian process with a second smoothness criteria, minimum set to the lower envelope, and maximum set to the upper envelope to produce the smooth estimate.

Example 15 may include the method of example 9, further comprising determining a difference between the smooth estimate and the composite signal, and producing a transient estimate for a transient component of the composite signal based on the difference between the smooth estimate and the composite signal.

Example 16 may include a vital monitor system, comprising a sensor to sense vital signs of an individual, and generate a composite signal based on the vital signs, and a device coupled to the sensor, the device to obtain the composite signal from the sensor, produce an upper envelope based on the composite signal in accordance with a smoothness parameter, produce a lower envelope based on the composite signal in accordance with the smoothness parameter, and produce a smooth estimate for a smooth component of the composite signal, wherein the smooth estimate is to be located between the upper envelope and the lower envelope, and wherein the smooth estimate corresponds to a vital sign of the vital signs.

Example 17 may include the vital monitor system of example 16, wherein the smoothness parameter is a first smoothness parameter, and wherein the smooth estimate is to be produced in accordance with a second smoothness parameter.

Example 18 may include the vital monitor system of example 16, wherein to produce the upper envelope includes setting a minimum for the upper envelope to the composite signal, and wherein the lower envelope includes setting a maximum of the lower envelope to the composite signal.

Example 19 may include the vital monitor system of example 16, wherein the device is further to determine a difference between the smooth estimate and the composite signal, and produce an estimate based on the difference between the smooth estimate and the composite signal.

Example 20 may include the vital monitor system of example 19, wherein the vital sign is respiration of the individual, and wherein the estimate corresponds to heart activity of the individual from the vital signs.

The foregoing outlines features of one or more embodiments of the subject matter disclosed herein. These embodiments are provided to enable a person having ordinary skill in the art (PHOSITA) to better understand various aspects of the present disclosure. Certain well-understood terms, as well as underlying technologies and/or standards may be referenced without being described in detail. It is anticipated that the PHOSITA will possess or have access to background knowledge or information in those technologies and standards sufficient to practice the teachings of the present disclosure.

The PHOSITA will appreciate that they may readily use the present disclosure as a basis for designing or modifying other processes, structures, or variations for carrying out the same purposes and/or achieving the same advantages of the embodiments introduced herein. The PHOSITA will also recognize that such equivalent constructions do not depart from the spirit and scope of the present disclosure, and that they may make various changes, substitutions, and alterations herein without departing from the spirit and scope of the present disclosure.

Note that the activities discussed above with reference to the FIGURES are applicable to any integrated circuit that involves signal processing (for example, gesture signal processing, video signal processing, audio signal processing, analog-to-digital conversion, digital-to-analog conversion), particularly those that can execute specialized software programs or algorithms, some of which may be associated with processing digitized real-time data. Certain embodiments can relate to multi-DSP, multi-ASIC, or multi-SoC signal processing, floating point processing, signal/control processing, fixed-function processing, microcontroller applications, etc. In certain contexts, the features discussed herein can be applicable to medical systems, scientific instrumentation, wireless and wired communications, radar, industrial process control, audio and video equipment, current sensing, instrumentation (which can be highly precise), and other digital-processing-based systems. Moreover, certain embodiments discussed above can be provisioned in digital signal processing technologies for medical imaging, patient monitoring, medical instrumentation, and home healthcare. This could include, for example, pulmonary monitors, accelerometers, heart rate monitors, or pacemakers, along with peripherals therefor. Other applications can involve automotive technologies for safety systems (e.g., stability control systems, driver assistance systems, braking systems, infotainment and interior applications of any kind). Furthermore, powertrain systems (for example, in hybrid and electric vehicles) can use high-precision data conversion, rendering, and display products in battery monitoring, control systems, reporting controls, maintenance activities, and others. In yet other example scenarios, the teachings of the present disclosure can be applicable in the industrial markets that include process control systems that help drive productivity, energy efficiency, and reliability. In consumer applications, the teachings of the signal processing circuits discussed above can be used for image processing, auto focus, and image stabilization (e.g., for digital still cameras, camcorders, etc.). Other consumer applications can include audio and video processors for home theater systems, DVD recorders, and high-definition televisions. Yet other consumer applications can involve advanced touch screen controllers (e.g., for any type of portable media device). Hence, such technologies could readily part of smartphones, tablets, security systems, PCs, gaming technologies, virtual reality, simulation training, etc.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

The particular embodiments of the present disclosure may readily include a system on chip (SoC) central processing unit (CPU) package. An SoC represents an integrated circuit (IC) that integrates components of a computer or other electronic system into a single chip. It may contain digital, analog, mixed-signal, and radio frequency functions: all of which may be provided on a single chip substrate. Other embodiments may include a multi-chip-module (MCM), with a plurality of chips located within a single electronic package and configured to interact closely with each other through the electronic package. Any module, function, or block element of an ASIC or SoC can be provided, where appropriate, in a reusable "black box" intellectual property (IP) block, which can be distributed separately without disclosing the logical details of the IP block. In various other embodiments, the digital signal processing functionalities may be implemented in one or more silicon cores in application-specific integrated circuits (ASICs), field-programmable gate arrays (FPGAs), and other semiconductor chips.

In some cases, the teachings of the present disclosure may be encoded into one or more tangible, non-transitory computer-readable mediums having stored thereon executable instructions that, when executed, instruct a programmable device (such as a processor or DSP) to perform the methods or functions disclosed herein. In cases where the teachings herein are embodied at least partly in a hardware device (such as an ASIC, IP block, or SoC), a non-transitory medium could include a hardware device hardware-programmed with logic to perform the methods or functions disclosed herein. The teachings could also be practiced in the form of Register Transfer Level (RTL) or other hardware description language such as VHDL or Verilog, which can be used to program a fabrication process to produce the hardware elements disclosed.

In example implementations, at least some portions of the processing activities outlined herein may also be implemented in software. In some embodiments, one or more of these features may be implemented in hardware provided external to the elements of the disclosed figures, or consolidated in any appropriate manner to achieve the intended functionality. The various components may include software (or reciprocating software) that can coordinate in order to achieve the operations as outlined herein. In still other embodiments, these elements may include any suitable algorithms, hardware, software, components, modules, interfaces, or objects that facilitate the operations thereof.

Additionally, some of the components associated with described microprocessors may be removed, or otherwise consolidated. In a general sense, the arrangements depicted in the figures may be more logical in their representations, whereas a physical architecture may include various permutations, combinations, and/or hybrids of these elements. It is imperative to note that countless possible design configurations can be used to achieve the operational objectives outlined herein. Accordingly, the associated infrastructure has a myriad of substitute arrangements, design choices, device possibilities, hardware configurations, software implementations, equipment options, etc.

Any suitably-configured processor component can execute any type of instructions associated with the data to achieve the operations detailed herein. Any processor disclosed herein could transform an element or an article (for example, data) from one state or thing to another state or thing. In another example, some activities outlined herein may be implemented with fixed logic or programmable logic (for example, software and/or computer instructions executed by a processor) and the elements identified herein could be some type of a programmable processor, programmable digital logic (for example, an FPGA, an erasable programmable read only memory (EPROM), an electrically erasable programmable read only memory (EEPROM)), an ASIC that includes digital logic, software, code, electronic instructions, flash memory, optical disks, CD-ROMs, DVD ROMs, magnetic or optical cards, other types of machine-readable mediums suitable for storing electronic instructions, or any suitable combination thereof. In operation, processors may store information in any suitable type of non-transitory storage medium (for example, random access memory (RAM), read only memory (ROM), FPGA, EPROM, electrically erasable programmable ROM (EEPROM), etc.), software, hardware, or in any other suitable component, device, element, or object where appropriate and based on particular needs. Further, the information being tracked, sent, received, or stored in a processor could be provided in any database, register, table, cache, queue, control list, or storage structure, based on particular needs and implementations, all of which could be referenced in any suitable timeframe. Any of the memory items discussed herein should be construed as being encompassed within the broad term 'memory.' Similarly, any of the potential processing elements, modules, and machines described herein should be construed as being encompassed within the broad term 'microprocessor' or 'processor.' Furthermore, in various embodiments, the processors, memories, network cards, buses, storage devices, related peripherals, and other hardware elements described herein may be realized by a processor, memory, and other related devices configured by software or firmware to emulate or virtualize the functions of those hardware elements.

Computer program logic implementing all or part of the functionality described herein is embodied in various forms, including, but in no way limited to, a source code form, a computer executable form, a hardware description form, and various intermediate forms (for example, mask works, or forms generated by an assembler, compiler, linker, or locator). In an example, source code includes a series of computer program instructions implemented in various programming languages, such as an object code, an assembly language, or a high-level language such as OpenCL, RTL, Verilog, VHDL, Fortran, C, C++, JAVA, or HTML for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

In one example embodiment, any number of electrical circuits of the FIGURES may be implemented on a board of an associated electronic device. The board can be a general circuit board that can hold various components of the internal electronic system of the electronic device and, further, provide connectors for other peripherals. More specifically, the board can provide the electrical connections by which the other components of the system can communicate electrically. Any suitable processors (inclusive of digital signal processors, microprocessors, supporting chipsets, etc.), memory elements, etc. can be suitably coupled to the board based on particular configuration needs, processing demands, computer designs, etc. Other components such as external storage, additional sensors, controllers for audio/video display, and peripheral devices may be attached to the board as plug-in cards, via cables, or integrated into the board itself. In another example embodiment, the electrical circuits of the FIGURES may be implemented as standalone modules (e.g., a device with associated components and circuitry configured to perform a specific application or function) or implemented as plug-in modules into application-specific hardware of electronic devices.

Note that with the numerous examples provided herein, interaction may be described in terms of two, three, four, or more electrical components. However, this has been done for purposes of clarity and example only. It should be appreciated that the system can be consolidated in any suitable manner. Along similar design alternatives, any of the illustrated components, modules, and elements of the FIGURES may be combined in various possible configurations, all of which are clearly within the broad scope of this disclosure. In certain cases, it may be easier to describe one or more of the functionalities of a given set of flows by only referencing a limited number of electrical elements. It should be appreciated that the electrical circuits of the FIGURES and its teachings are readily scalable and can accommodate a large number of components, as well as more complicated/sophisticated arrangements and configurations. Accordingly, the examples provided should not limit the scope or inhibit the broad teachings of the electrical circuits as potentially applied to a myriad of other architectures.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke 35 U.S.C. § 112(f) as it exists on the date of the filing hereof unless the words "means for" or "steps for" are specifically used in the particular claims; and (b) does not intend, by any statement in the disclosure, to limit this disclosure in any way that is not otherwise reflected in the appended claims.

What is claimed is:

1. One or more non-transitory computer-readable media having instructions stored thereon, wherein the instructions, when executed by processing circuitry of a vital monitor system, perform the steps of:

sensing multiple characteristics of an individual by a sensor of the vital monitor system;

generate a composite signal based on the multiple characteristics;

producing an upper envelope for the composite signal, wherein producing the upper envelope includes setting a minimum value permitted for the upper envelope, the minimum value being equal to the composite signal;

producing a lower envelope for the composite signal, wherein producing the lower envelope includes setting a maximum value permitted for the lower envelope, the maximum value being equal to the composite signal, and wherein the composite signal is decomposed into multiple signals corresponding to respective different characteristics sensed by the sensor configured to sense vital signs of an individual, with a first characteristic of the respective different characteristic being respiration of an individual;

producing a smooth estimate for a smooth component of the composite signal, the smooth estimate being located between the upper envelope and the lower envelope, wherein producing the smooth estimate comprises solving a minimization problem with respect to a function based on a distance of the smooth estimate from the composite signal;

identifying the smooth estimate with the respiration of the individual; and providing an output based on the smooth estimate for monitoring at least one of the multiple characteristics of the individual, wherein to provide the output, the instructions, when executed by the processing circuitry, further cause the processing circuitry to indicate a current physiological parameter of the individual.

2. The one or more non-transitory computer-readable media of claim 1, wherein:

producing the upper envelope includes producing a first curve with lower limits set by the composite signal; and producing the lower envelope includes producing a second curve with upper limits set by the composite signal.

3. The one or more non-transitory computer-readable media of claim 2, wherein:

producing the upper envelope includes:

minimizing a distance between the first curve and the composite signal; and adding a first smoothness parameter to the first curve; and producing the lower envelope includes:

minimizing a distance between the second curve and the composite signal; and adding a second smoothness parameter to the second curve.

4. The one or more non-transitory computer-readable media of claim 3, wherein the first smoothness parameter for the upper envelope is different from the second smoothness parameter for the lower envelope.

5. The one or more non-transitory computer-readable media of claim 1, wherein the instructions, when executed by the processing circuitry, further cause the processing circuitry to:

set a smoothness parameter, wherein a smoothness of the smooth estimate is based on the smoothness parameter.

6. The one or more non-transitory computer-readable media of claim 1, wherein the instructions, when executed by the processing circuitry, further cause the processing circuitry to:

set a smoothness parameter, wherein a smoothness of the upper envelope and a smoothness of the lower envelope is based on the smoothness parameter.

7. The one or more non-transitory computer-readable media of claim 1, wherein:

producing the upper envelope further includes solving a first minimization problem utilizing a first Gaussian process with a smoothness parameter and the minimum value permitted for the upper envelope; and producing the lower envelope further includes solving a second minimization problem utilizing a second Gaussian process with the smoothness parameter and the maximum value permitted for the lower envelope.

8. The one or more non-transitory computer-readable media of claim 1, wherein solving the minimization problem comprises utilizing a Gaussian process having a smoothness parameter, a minimum value permitted for the smooth estimate set to the lower envelope, and a maximum value permitted for the smooth estimate set to the upper envelope.

9. The one or more non-transitory computer-readable media of claim 1, wherein the instructions, when executed by the processing circuitry, further cause the processing circuitry to:

generate a transient estimate for a transient component of the composite signal based on a difference between the smooth estimate and the composite signal.

10. The one or more non-transitory computer-readable media of claim 9, wherein a second characteristic of the respective different characteristic is heart activity of the individual, and wherein the instructions, when executed by the processing circuitry, further cause the processing circuitry to identify the transient estimate with the heart activity of the individual.

11. The one or more non-transitory computer-readable media of claim 1, wherein the current physiological parameter of the individual includes at least one of a respiration parameter of the individual and a heart activity parameter of the individual.

* * * * *